(12) United States Patent
Boinot

(10) Patent No.: US 7,645,138 B2
(45) Date of Patent: Jan. 12, 2010

(54) DEVICE FOR LOCKING A DENTAL INSTRUMENT ON A HANDPIECE CONSISTING OF A ROTATING SPINDLE, LOCKING SPRING AND PUSH-BUTTON ASSEMBLY

(75) Inventor: Jean-Claude Boinot, Rigney (FR)

(73) Assignee: Micro Mega International Manufactures (Societe Anonyme), Besancon (FR)

( * ) Notice: Subject to any disclaimer, the term of this patent is extended or adjusted under 35 U.S.C. 154(b) by 138 days.

(21) Appl. No.: 11/817,498

(22) PCT Filed: Jan. 11, 2006

(86) PCT No.: PCT/FR2006/000050

§ 371 (c)(1), (2), (4) Date: Aug. 30, 2007

(87) PCT Pub. No.: WO2006/097587

PCT Pub. Date: Sep. 21, 2006

(65) Prior Publication Data

US 2008/0187884 A1 Aug. 7, 2008

(30) Foreign Application Priority Data

Mar. 14, 2005 (FR) ................... 05 02464

(51) Int. Cl.
*A61C 1/14* (2006.01)
(52) U.S. Cl. ..................................... 433/128
(58) Field of Classification Search ......... 433/125–129; 279/76, 79, 82, 93
See application file for complete search history.

(56) References Cited

U.S. PATENT DOCUMENTS

| 4,370,132 A * | 1/1983 | Wohlgemuth | 433/128 |
| 5,704,786 A * | 1/1998 | Quinn | 433/128 |
| 2004/0014005 A1 * | 1/2004 | Kuhn | 433/127 |

FOREIGN PATENT DOCUMENTS

FR 891672 3/1944

* cited by examiner

*Primary Examiner*—Cris L Rodriguez
*Assistant Examiner*—Matthew M Nelson
(74) *Attorney, Agent, or Firm*—Egbert Law Offices PLLC

(57) ABSTRACT

The invention concerns a device for locking a dental instrument having a rotating spindle, formed by a hollow spindle and adapted to receive the head of an instrument, and a locking spring formed by a lower ring extending on a common side by two branches or a plurality of elastic branches. Each branch is provided with a pin engaged in an annular groove provided in the head of the instrument. There is a push-button having, in its underside, a central conical pressure head adapted to space apart radially the branches of the locking spring to release the pins from the annular groove of the instrument. The locking branches are housed in the slots provided in the rotary spindle to lock in rotation the spring relative to the rotary spindle, the spring being moreover maintained axially between the push-button and a shoulder of the rotary spindle.

5 Claims, 2 Drawing Sheets

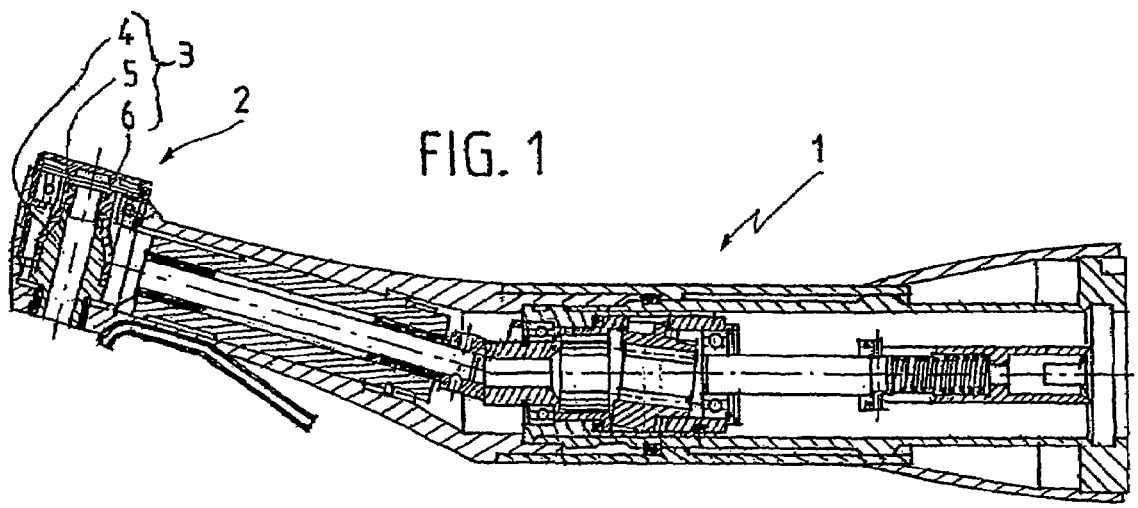
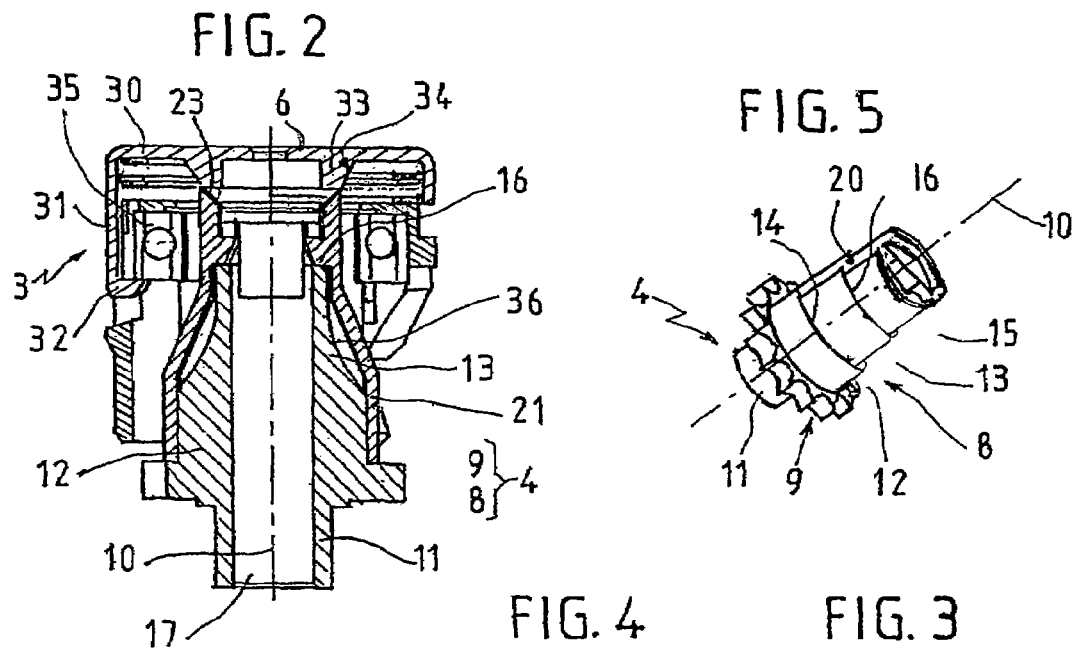
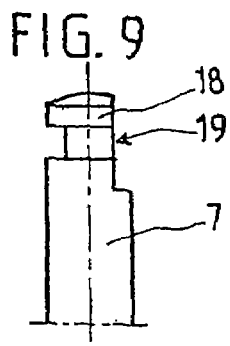

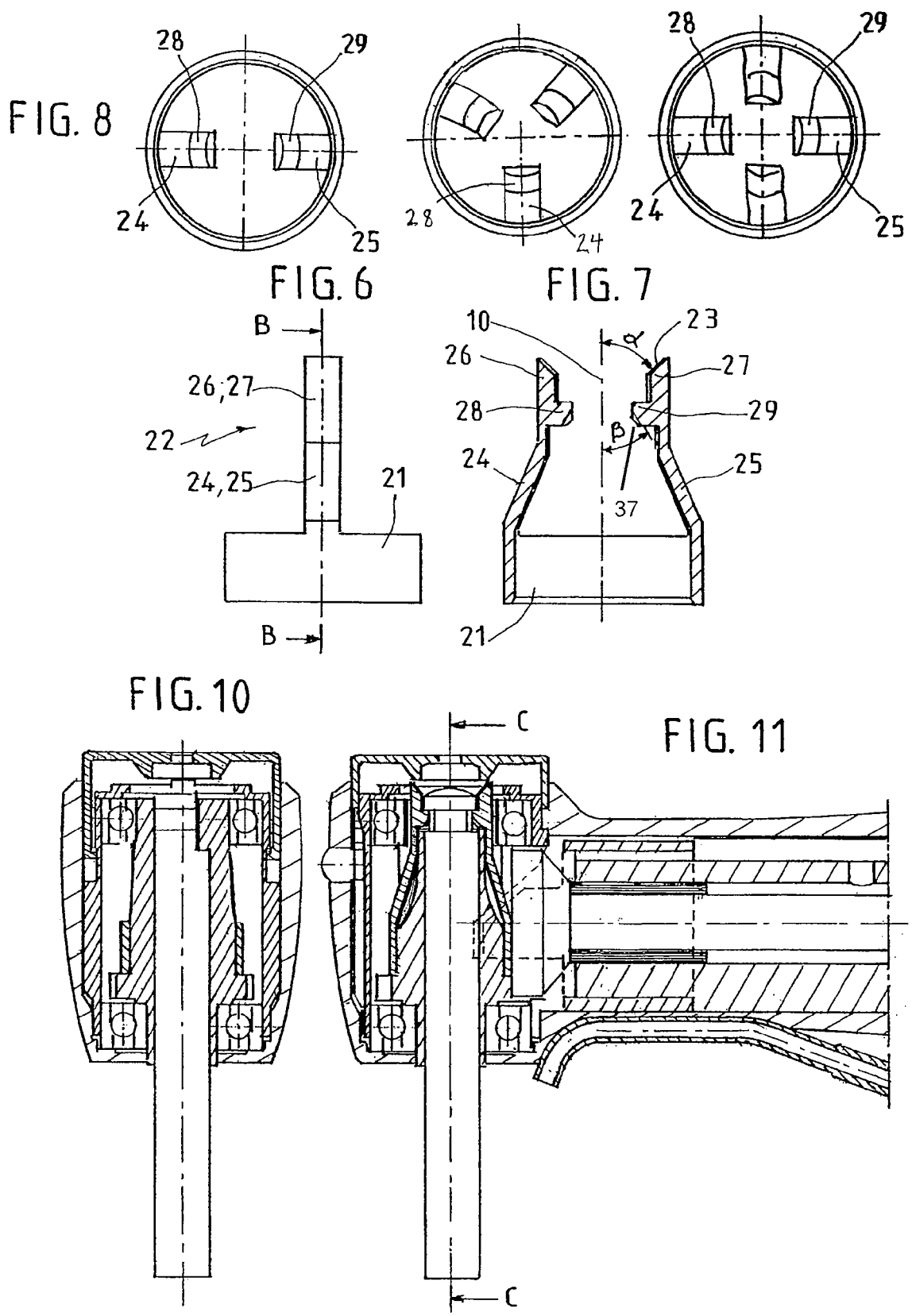

DEVICE FOR LOCKING A DENTAL INSTRUMENT ON A HANDPIECE CONSISTING OF A ROTATING SPINDLE, LOCKING SPRING AND PUSH-BUTTON ASSEMBLY

CROSS-REFERENCE TO RELATED U.S. APPLICATIONS

Not applicable.

STATEMENT REGARDING FEDERALLY SPONSORED RESEARCH OR DEVELOPMENT

Not applicable.

NAMES OF PARTIES TO A JOINT RESEARCH AGREEMENT

Not applicable.

REFERENCE TO AN APPENDIX SUBMITTED ON COMPACT DISC

Not applicable.

BACKGROUND OF THE INVENTION

1. Field of the Invention

The present invention concerns a novel device for locking a dental instrument.

2. Description of Related Art Including Information Disclosed Under 37 CFR 1.97 and 37 CFR 1.98.

An object of the invention is to allow an instrument to be locked on the drive elements of the head of a dental handpiece without requiring the use of particular tools, and by means of an easy-to-use spring system.

BRIEF SUMMARY OF THE INVENTION

This object is achieved by a device for locking a dental instrument, of the type comprising a body that accommodates motorization elements and/or movement-transmitting elements, and a tool-holder head, said device being characterized in that it is composed of a rotary spindle, a locking spring and a push-button.

The rotary spindle is formed by a hollow spindle adapted to mesh with the movement-transmitting elements of the handpiece and being traversed longitudinally by an open central bore adapted to receive the head of an instrument.

The locking spring is formed by a lower ring positioned around the hollow spindle and continued on a common side by two arms, or a plurality of elastic arms, each provided with a pin and each having a rest position, in which the pin engages in an annular groove provided on the head of the instrument, and a spaced-apart position, in which the pin is moved away from the central axis for the purpose of its release.

The cap-shaped push-button comprises, on its underside, a central and conical pressure head with an external slope which, when the user presses the push-button in the direction of the instrument, is able to space the arms of the locking spring radially apart in order to release the pins from the annular groove of the instrument.

In addition, the locking arms are housed in slots provided in the rotary spindle, so as to block the spring in rotation relative to the rotary spindle, the spring also being maintained axially between the push-button and a shoulder of the rotary spindle.

BRIEF DESCRIPTION OF THE SEVERAL VIEWS OF THE DRAWINGS

The invention will be better understood on reading the following description in which reference is made to the following attached figures.

FIG. 1 is a longitudinal sectional view of a dental handpiece for endodontic work, equipped with a spring-type locking device according to the invention.

FIG. 2 is a longitudinal sectional view of the locking device according to the invention.

FIG. 3 is a side elevation view of the rotary spindle of the locking device from FIGS. 1 and 2, equipped with a spring according to the invention.

FIG. 4 is a sectional view along A-A in FIG. 3.

FIG. 5 is a perspective view of the rotary spindle from FIG. 3.

FIGS. 6, 7 and 8 are, respectively, a side view, a sectional view along B-B, and a bottom view of the spring from FIGS. 1 to 4.

FIG. 9 is a side view of the shaft of an instrument adapted to cooperate with the locking device according to the invention.

FIGS. 10 and 11 are a longitudinal sectional view and a sectional view along C-C, depicting an instrument engaged in a locking device according to the invention.

DETAILED DESCRIPTION OF THE INVENTION

FIG. 1 shows a dental instrument comprising a body (1) that accommodates motorization elements and/or movement-transmitting elements (which are conventional and are not shown here), and a tool-holder head (2).

The head(2) has a locking device (3) according to the invention, composed of a rotary spindle (4), a locking spring (5) and a push-button (6) (see FIGS. 1 and 2 in particular), and it is designed to cooperate with a tool whose shaft (7) is of the type depicted in FIGS. 9 to 11.

The rotary spindle (4) shown in FIGS. 1 to 8 is formed by a hollow spindle (8) which carries, perpendicular to its central axis (10), a pinion (9) adapted to mesh in a conventional manner with the movement-transmitting elements of the handpiece.

The hollow spindle (8) is continued, on the underside of the pinion (9), by a cylindrical sleeve (11) adapted to cooperate in a conventional manner with a roller bearing (FIGS. 10, 11) or a bearing (FIG. 1).

The hollow spindle (8) comprises, above the pinion (9) (see FIGS. 5 and 2), a cylindrical lower part (12) followed toward the top by a central part (13) of smaller diameter than the lower part and separated from the latter by a peripheral shoulder (14), then a cylindrical upper part (15) of smaller diameter than the central part (13) and separated from the latter by a peripheral shoulder (16).

The hollow spindle (8) is traversed longitudinally by an open central bore (17) receiving the shaft (7) whose head is equipped in a conventional manner with an annular groove (18) for axial blocking by virtue of the pins, and with a flat surface (19) parallel to the longitudinal axis of the shaft for blocking in rotation by a corresponding flat surface of the hollow spindle.

The hollow spindle comprises a slot (20) on its upper and central parts. Said slot (20) diametrically crosses the upper part

(15) and the central bore (17) and opens to the outside on each side. This slot is continued downward by two cuttings that open to the outside along the entire height of the central part (13) and are of the same width as the slot and have a base with a concavely curved profile (36) visible in FIG. 4.

The spring (5) (see FIGS. 6 to 8) is formed by a lower ring (21) that supports, on one side, two diametrically opposite elastic arms (22) or several arms distributed uniformly on the periphery of said ring.

Each arm comprises, starting from the ring, a central segment (24) or (25) inclined in the direction of the central axis (10) and terminated by an upper segment (26) or (27) parallel to said axis (10), each one terminated by an internal slope (23) inclined by an angle a toward the top (45° for example, see FIG. 7). Each upper segment (26) or (27) supports, in the direction of the central axis (10), a transverse pin (28) or (29) adapted to snap into the annular groove (18) of the instrument shaft (see assembly in FIG. 4 or FIGS. 10 and 11) and comprising a plane (37) inclined toward the bottom by an angle β (30° for example, see FIG. 7).

The ring (21) is positioned and applied around the lower part (12) of the hollow spindle (FIG. 2), the inclined segments (24, 25) are placed externally of the central part (13) of said hollow spindle without coming into contact with it, because of its concave profile (36), while the segments (26) and (27) take up position in the slot (20) of the upper part (15) of the hollow spindle, and the pins (29) snap into the groove (18) of the instrument (FIGS. 9, 10, 11).

The push-button (6) according to the variant in FIGS. 1 and 2 is conventionally cap-shaped with a circular flat face (30) provided with an annular peripheral spindle skirt (31) that is bordered by a perpendicular collar (32) directed toward the axis (10), so as to lock, for example, under a roller bearing (35) of the head (2) and serve as an upper axial abutment for the push-button.

Said push-button comprises, on its underside, a central and conical pressure head (33) with an external slope (34) which, when the face (30) is pressed in the direction of the instrument, is able to engage between the two segments (26, 27) of the spring, by sliding on the two internal inclined surfaces (23), and is able to space said segments radially outward in order to release the pins (28, 29) from the groove and free the instrument.

An instrument is locked by introducing the tool head into the central bore (17) and moving it in the direction of the push-button. The inclined surfaces (37) of the pins (28, 29) promote the sliding of the tool head and the spacing-apart of the pins and arms as said head passes them, and the elasticity of the arms then allows them to return to the rest position and snap into the groove (20).

The variant in FIGS. 10 and 11 shows that other embodiments are possible without departing from the scope of the invention.

Likewise, it is possible to provide three or four elastic arms on the spring (5) without departing from the scope of the invention, in which case the hollow spindle will comprise three or four radial slots distributed at 120° or at 90°, respectively, or two perpendicular diametrical slots.

The locking device according to the invention is easy to use and does not require a special tool for fitting or removing the instrument, and the spring element is mounted on the rotary spindle without requiring any special fixation.

The invention claimed is:

1. A dental tool assembly comprising:
    a housing body having a plurality of motorization means contained therein and a tool-holder head at one end thereof;
    a dental instrument or tool, said dental instrument being comprised of a shaft with an annular groove at one end thereof and having a flat surface in said annular groove parallel to a longitudinal axis of said shaft;
    a rotary spindle being comprised of a hollow spindle and a pinion, said hollow spindle having an open central bore traversing said hollow spindle longitudinally, the central bore receiving said dental instrument therein, said pinion being perpendicular to a central axis of said hollow spindle and meshing with said motorization means, said hollow spindle comprising:
        a cylindrical sleeve, being mounted below said pinion and cooperative with a bearing;
        a cylindrical lower part, being mounted above said pinion;
        a central part, being positioned above said cylindrical lower part, having a diameter smaller than a diameter of said cylindrical lower part, and forming a first peripheral shoulder on said cylindrical lower part;
        a cylindrical upper part, being positioned above said central part, having a diameter smaller than said diameter of said central part, and forming a second peripheral shoulder on said central part; and
        a slot, being located on the upper part and the central part, diametrically crossing the upper part and the central bore, and opening outward on each side of said hollow spindle, said slot continuing downward by two cuttings open outwardly along the central part, said two cuttings being aligned and having an identical width as said slot in the upper part, said slot having a concavely curved profile corresponding to curvature of the upper part;
    a locking spring, being comprised of a lower ring positioned around said hollow spindle and a plurality of elastic arms extending from one side of said lower ring, each arm being provided with a pin and having a rest position and a spaced-apart position, said pin engaging said annular groove of said dental instrument in said rest position, said pin being displaced away from said central axis of said hollow spindle in said spaced-apart position so as to release said dental instrument, each arm comprising:
        a central segment having one end attached to said lower ring and being inclined in a direction towards said central axis of said hollow spindle; and
        an upper segment parallel to said central axis at a terminal end of the arm, said central segment extending from said lower ring to said upper segment, each segment having an internal slope inclined by an angle towards the terminal end thereof; and
    a cap-shaped push-button comprising a center conical pressure head on an underside thereof, the pressure head having an external slope engaging the arms of said locking spring, the pins being moved from said rest position to said spaced apart position when the push-button is depressed towards said dental instrument such that the pins release said annular groove of said dental instrument.

2. The dental tool assembly, according to claim 1, wherein the elastic arms are housed in the slot of said rotary spindle.

3. The dental tool assembly, according to claim 1, wherein the number of elastic arms of said locking spring corresponds to the number of slots in said hollow spindle, the arms and slots being evenly distributed around a circumference of the respective lower ring of said locking spring and the cylindrical central and upper parts.

4. The dental tool assembly, according to claim 1, wherein said upper segment of the elastic arm supports a transverse pin in snap-fit relation to said annular groove of the dental instrument in said rest position, said transverse pin being oriented in a direction toward the central axis of said hollow spindle, said transverse pin having a bottom plane inclined at an angle from said central axis of said hollow spindle toward a bottom end thereof.

5. The dental tool assembly device, according to claim 1, wherein the push-button has a cap shape with a circular flat face provided with an annular peripheral spindle skirt, the spindle skirt being bordered by a perpendicular collar directed toward said central axis of said hollow spindle and locked under a roller bearing of said tool-holder head, said perpendicular collar forming an upper axial abutment engaging said roller bearing.

* * * * *